(12) United States Patent
Chang et al.

(10) Patent No.: US 9,186,180 B2
(45) Date of Patent: Nov. 17, 2015

(54) ROSE GEAR FOR EXTERNAL FIXATION CLAMP

(71) Applicant: Stryker Trauma SA, Selzach (CH)

(72) Inventors: Eric Chang, East Brunswick, NJ (US); Beat Mürner, Reichenbach (CH)

(73) Assignee: Stryker Trauma SA (CH)

( * ) Notice: Subject to any disclaimer, the term of this patent is extended or adjusted under 35 U.S.C. 154(b) by 147 days.

(21) Appl. No.: 13/790,441

(22) Filed: Mar. 8, 2013

(65) Prior Publication Data

US 2014/0257287 A1    Sep. 11, 2014

(51) Int. Cl.
*A61B 17/00* (2006.01)
*A61B 17/66* (2006.01)
*A61B 17/64* (2006.01)

(52) U.S. Cl.
CPC .............. *A61B 17/66* (2013.01); *A61B 17/6466* (2013.01); *A61B 17/6475* (2013.01)

(58) Field of Classification Search
USPC ........................................ 606/54–59, 90, 105
See application file for complete search history.

(56) References Cited

U.S. PATENT DOCUMENTS

| | | | |
|---|---|---|---|
| 1,136,069 A | 4/1915 | Weaver | |
| 1,683,758 A | 9/1928 | Candee | |
| 1,694,028 A | 12/1928 | Wildhaber | |
| 2,062,700 A | 12/1936 | Christman | |
| 2,089,732 A | 8/1937 | Christman | |
| 2,930,248 A | 3/1960 | Wildhaber | |
| 3,768,326 A | 10/1973 | Georgiev et al. | |
| 4,321,022 A | 3/1982 | Zimmern | |
| 4,342,548 A | 8/1982 | Zimmern | |
| 4,488,542 A * | 12/1984 | Helland | 606/59 |
| 4,782,842 A * | 11/1988 | Fietti, Jr. | 606/54 |
| 4,926,712 A | 5/1990 | Stritzel | |
| 4,988,244 A | 1/1991 | Sheldon et al. | |
| 5,664,457 A * | 9/1997 | Nejati | 74/110 |
| 6,128,969 A | 10/2000 | Litvin et al. | |
| 6,148,683 A | 11/2000 | Fleytman | |
| 6,398,532 B1 | 6/2002 | Zha et al. | |
| 6,447,418 B1 | 9/2002 | Fleytman | |
| 6,523,430 B1 | 2/2003 | Fleytman | |

(Continued)

FOREIGN PATENT DOCUMENTS

FR   2954904 A1   7/2011
WO   2009018349 A2   2/2009

(Continued)

OTHER PUBLICATIONS

Extended European Search Report for Application No. EP14154577 dated May 30, 2014.

*Primary Examiner* — Eduardo C Robert
*Assistant Examiner* — Steven Cotroneo
(74) *Attorney, Agent, or Firm* — Lerner, David, Littenberg, Krumholz & Mentlik, LLP

(57) ABSTRACT

Disclosed herein are external fixation devices including at least an elongate rod, a housing and an actuation member. The housing is coupled to the elongate rod and the actuation member is rotatably coupled to the housing such that a central longitudinal axis of the actuation member is angled and offset with respect to a central longitudinal axis of the elongate rod. Rotation of an actuation portion of the actuation member about the central longitudinal axis thereof in a first radial direction causes the housing to translate along the central longitudinal axis of the elongate rod in a first direction.

21 Claims, 8 Drawing Sheets

(56) References Cited

U.S. PATENT DOCUMENTS

| | | |
|---|---|---|
| 6,537,174 B2 | 3/2003 | Fleytman |
| 6,912,786 B2 | 7/2005 | Jinkins et al. |
| 6,916,140 B2 | 7/2005 | Fleytman |
| 6,972,020 B1 * | 12/2005 | Grayson et al. ............... 606/90 |
| 7,377,195 B2 | 5/2008 | Fleytman |
| 7,421,922 B2 | 9/2008 | Hamann et al. |
| 7,422,593 B2 | 9/2008 | Cresina et al. |
| 7,449,023 B2 | 11/2008 | Walulik et al. |
| 7,468,063 B2 | 12/2008 | Walulik et al. |
| 7,507,240 B2 * | 3/2009 | Olsen ............................. 606/59 |
| 7,552,662 B2 | 6/2009 | Pardo |
| 7,707,721 B2 | 5/2010 | Leibold |
| 8,133,146 B2 | 3/2012 | Radzevich et al. |
| 8,333,766 B2 | 12/2012 | Edelhauser et al. |
| 8,372,081 B1 * | 2/2013 | Schafer et al. ................. 606/90 |
| 2004/0221672 A1 * | 11/2004 | Fleytman .......................... 74/425 |
| 2006/0005653 A1 | 1/2006 | Fleytman |
| 2006/0229605 A1 * | 10/2006 | Olsen ............................. 606/54 |
| 2007/0012491 A1 * | 1/2007 | Vasta ........................... 180/65.1 |
| 2008/0087124 A1 | 4/2008 | Fleytman |
| 2009/0000120 A1 | 1/2009 | Shiino et al. |
| 2010/0312243 A1 * | 12/2010 | Ross et al. ...................... 606/56 |
| 2010/0317480 A1 | 12/2010 | Cochren et al. |
| 2011/0118738 A1 | 5/2011 | Vasta et al. |
| 2011/0125162 A1 * | 5/2011 | Noon et al. ................... 606/105 |
| 2012/0000305 A1 | 1/2012 | Kazkaz et al. |
| 2012/0316561 A1 * | 12/2012 | Dubois .......................... 606/58 |

FOREIGN PATENT DOCUMENTS

| | | |
|---|---|---|
| WO | 2009100459 A1 | 8/2009 |
| WO | 2011038108 A2 | 3/2011 |

* cited by examiner

ROSE GEAR FOR EXTERNAL FIXATION CLAMP

FIELD OF THE INVENTION

The present invention relates to mechanisms for manipulating external fixation systems and in particular relates to gear mechanisms for translating a threaded rod coupled to external fixation devices in order to manipulate the devices in a desired manner.

BACKGROUND OF THE INVENTION

Many different types of bone deformities can be corrected using external fixation systems. Such systems generally use rings, fixation plates, threaded rods or struts for manipulation, angulation, and translation of the bone deformities.

Existing fixation systems on the market have many components thereof that are static and do not allow for certain adjustment and/or pivoting. Lack of flexibility in a fixation system may restrict attachment to certain bone areas at certain angles as well as restrict motion of the portion of the body that the external fixation system is being attached to in order to correct. Because of such lack of flexibility, such systems may make it more difficult for the physician to achieve an optimal clinical outcome.

External fixation devices have been used to stabilize, distract and compress bone fragments of long bones such as the tibia and femur, for example. There also exists a need to manipulate the positions of couplings connected to rods of such external fixation devices. For instance, a first rod of an external fixation device may be coupled to a first bone fragment via a first cross-pin connected to the first rod by a coupling mechanism while a second rod may be coupled to a second bone fragment via a second cross-pin connected to the second rod by another coupling mechanism. Additional coupling mechanism may be used to connect the first and second rods. After such an external fixation system is connected to the bones that it is treating, the coupling mechanisms may have to be moved along their coupled positions on the rods in order to provide distraction and/or compression to the bones.

There exists a need for an integrated external fixation device that can be used to manipulate the positions of such coupling mechanisms. Access to actuating the integrated external fixation device would be easy as it is used to guide the movement of the coupling mechanism while load transfer occurs through the external fixation device.

It is known to use gears in external fixation systems to transmit torque applied to the gear to another component of the system. Conventional worm gears, for example, require the axis of the driving worm gear to be tangent or parallel to the driven gear. This limits the configuration of gear designs as well as the configuration of external fixation systems using these gears. Clutches or ratchets may be used to prevent backdrive; however, the addition of these devices increases the number of components needed to provide or restrict the motion of such gears.

BRIEF SUMMARY OF THE INVENTION

The present invention is for a novel "rose" gear design. The rose gear disclosed herein has a thread profile on a conical section of an actuation member. The gear design retains the self locking nature and high mechanical advantage of a worm drive while allowing for an angled driving gear. The gear design disclosed herein allows for an angled worm. The rotation of the rose gear drives the gear mated to it. This gear can either be a normal gear, rack, or threaded rod, resulting in both linear as well as rotational motion.

A first aspect of the present invention is an external fixation device comprising an elongate rod, a housing and an actuation member. The housing is coupled to the elongate rod. The actuation member is rotatably coupled to the housing such that a central longitudinal axis of the actuation member is angled and offset with respect to a central longitudinal axis of the elongate rod. The actuation member has a gear portion and an actuation portion, wherein rotation of the actuation portion of the actuation member about the central longitudinal axis thereof in a first radial direction causes the housing to translate along the central longitudinal axis of the elongate rod in a first direction.

In one embodiment according to this first aspect of the present invention, rotation of the actuation portion of the actuation member about the central longitudinal axis thereof in a second radial direction opposite the first radial direction causes the housing to translate along the central longitudinal axis of the elongate rod in a second direction opposite the first direction.

In another embodiment according to this first aspect, the gear portion of the actuation member is located at a distal portion of the actuation member and the actuation portion is located at a proximal portion of the actuation member.

In yet another embodiment of this first aspect, gear portion has a plurality of tooth portions extending from a central portion of the gear portion adjacent the central longitudinal axis of the actuation member towards an outer periphery of the gear portion. Each of the plurality of tooth portions are preferably curved in a first direction from the central portion of the gear portion towards the outer periphery of the gear portion. Further, each of the plurality of tooth portions are preferably curved in a second direction from the distal portion of the actuation member towards the proximal portion of the actuation member.

In still yet another embodiment of this first aspect, each of the plurality of tooth portions has first and second contact surfaces, the first and second contact surfaces being angled with respect to one another, wherein one of the first and second contact surfaces has a longitudinal axis parallel to the central longitudinal axis of the actuation member. The first and second contact surfaces are preferably flat.

In still yet another embodiment of this first aspect, the gear portion includes four tooth portions extending from the central portion of the gear portion separated 90° from one another about the longitudinal central axis of the actuation member. Preferably, the gear portion of the actuation member is substantially circular.

In still yet another embodiment of this first aspect, the housing has first and second bores, the elongate rod being at least partially received in the first bore when the elongate rod is coupled to the housing and the actuation member being at least partially received in the second bore when the housing is rotatably coupled to the housing. Preferably, each of the first and second bores has a longitudinal axis, the longitudinal axes of the first and second bores being angled and offset with respect to one another.

A second aspect of the present invention is an external fixation device comprising a housing, an elongate rod and an actuation member. The housing has first and second bores each having a longitudinal axis, the longitudinal axes of the first and second bores being angled and offset with respect to one another. The elongate rod has a central longitudinal axis and is at least partially received in the first bore of the housing. The actuation member has a central longitudinal axis and is at least partially received in the second bore of the housing. The actuation member has a gear portion and an actuation portion, wherein rotation of the actuation portion of the actuation member about the central longitudinal axis thereof in a first radial direction causes the housing to translate along the central longitudinal axis of the elongate rod in a first direction.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION

Referring to FIGS. 1-6, there is shown an embodiment of an external fixation device 100 having an elongate rod 200, a housing 300 and an actuation member 400.

Figure 1:
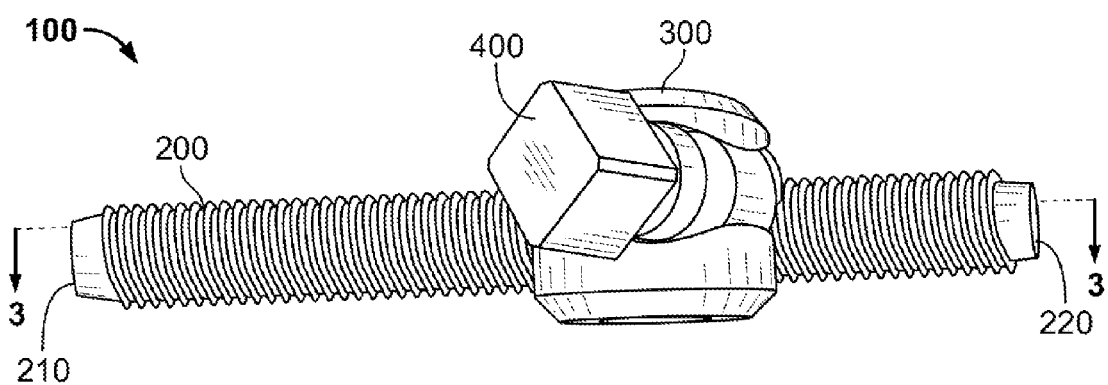
FIG. 1 is a perspective assembled view of one embodiment of an external fixation device of the present invention.
Figure 2:
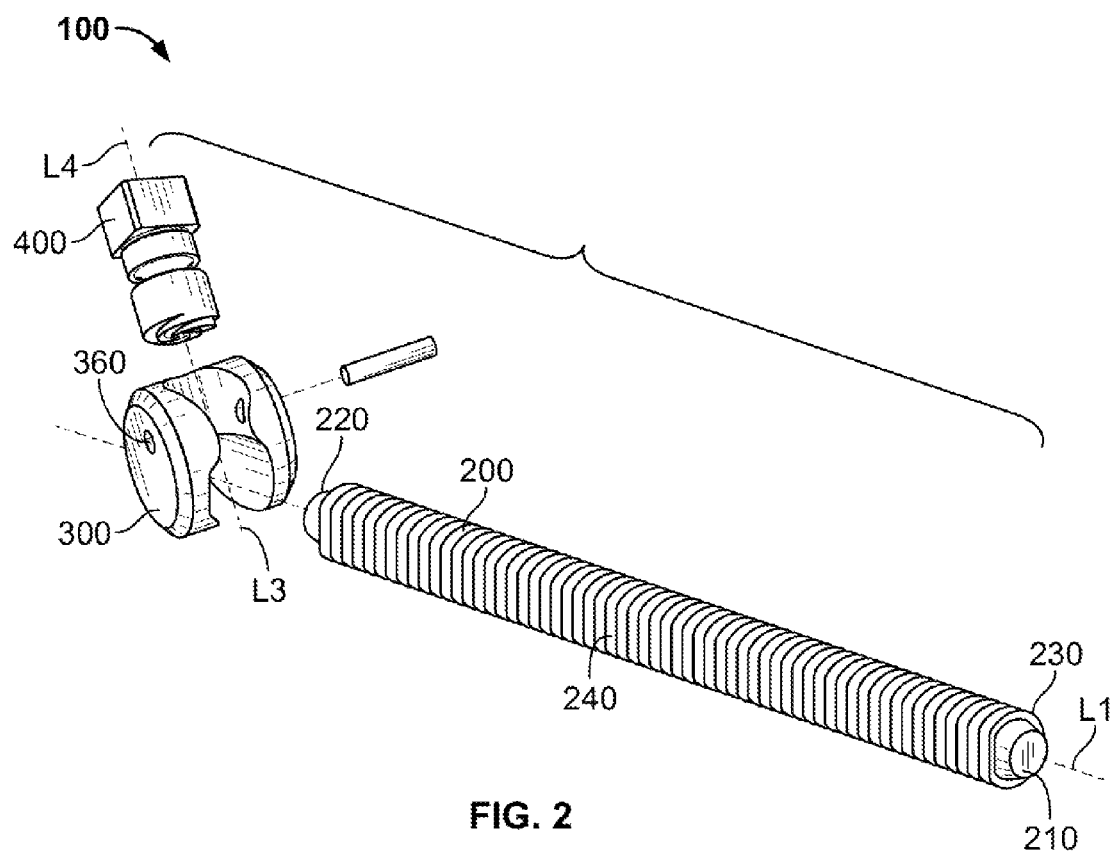
FIG. 2 is a perspective exploded view of the external fixation device of FIG. 1.
Figure 3:
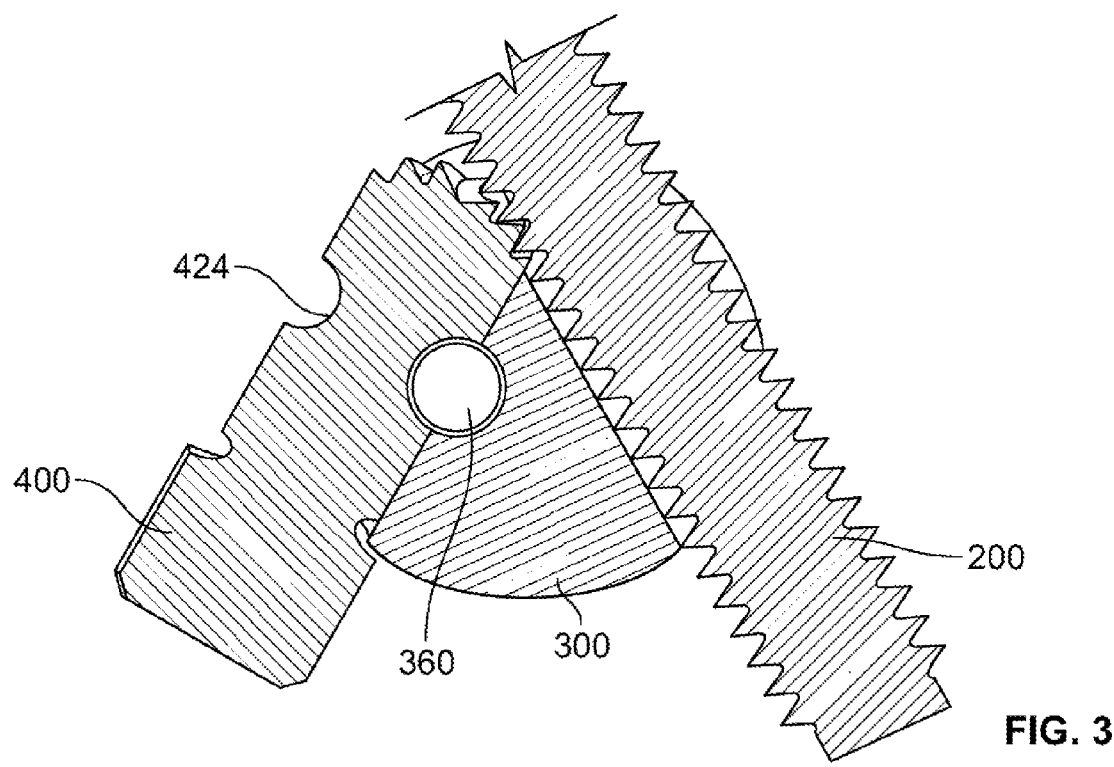
FIG. 3 is a cross-sectional view of the external fixation device taken along line 3-3 of FIG. 1.

As shown in FIGS. 1 and 2, elongate rod 200 has a distal end 210 and a proximal end 220 and is threaded along at least a portion of its length between the distal and proximal ends 210, 220 thereof. Elongate rod 200 has a longitudinal axis L1. The circumference of elongate rod 200 has a circular portion 230 and a flat portion 240. The distal and proximal ends 210, 220 are preferably chamfered or radiused such that elongate rod 200 does not have sharp ends. The chamfered or radiused ends of elongate rod 200 preferably aid in the coupling of additional external fixation device constructs to external fixation device 100. Such additional constructs are described later herein.

Figure 4A:
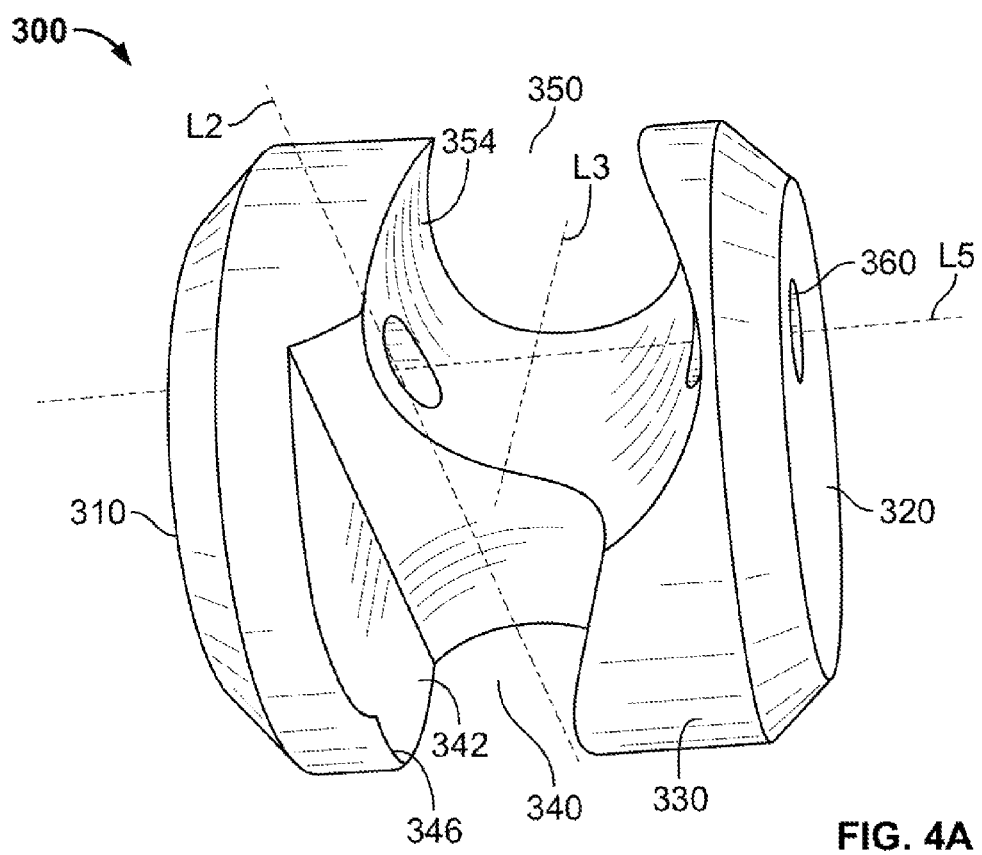
FIG. 4A is a perspective view of the housing shown in FIG. 1.
Figure 4B:
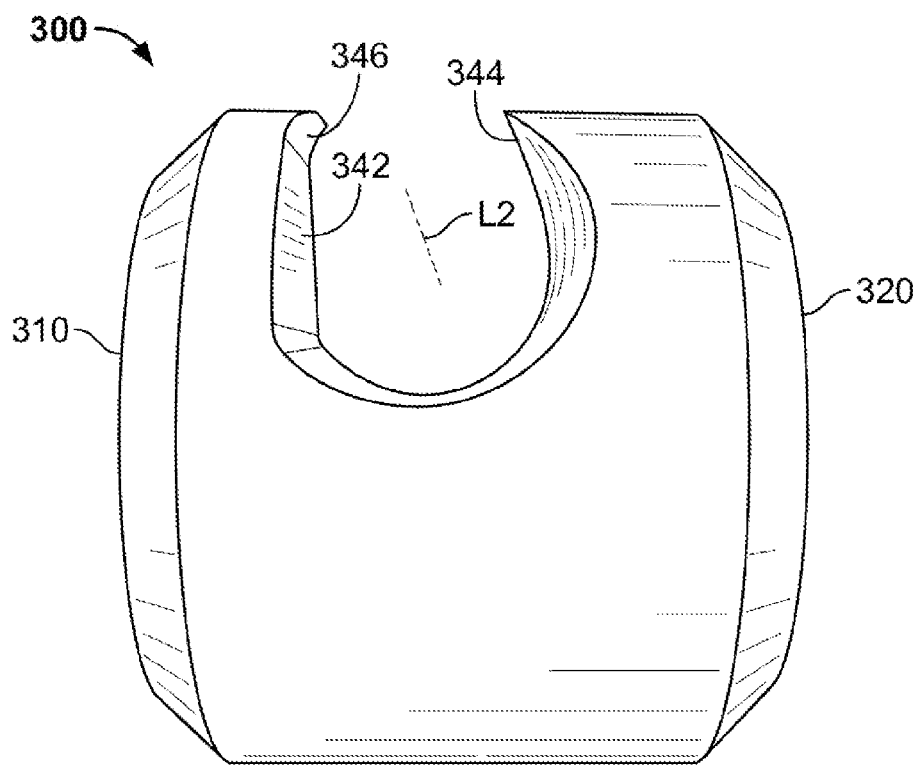
FIG. 4B is a plan view of the housing shown in FIG. 4A in which a bore for receiving the elongate rod therethrough is shown.
Figure 4C:
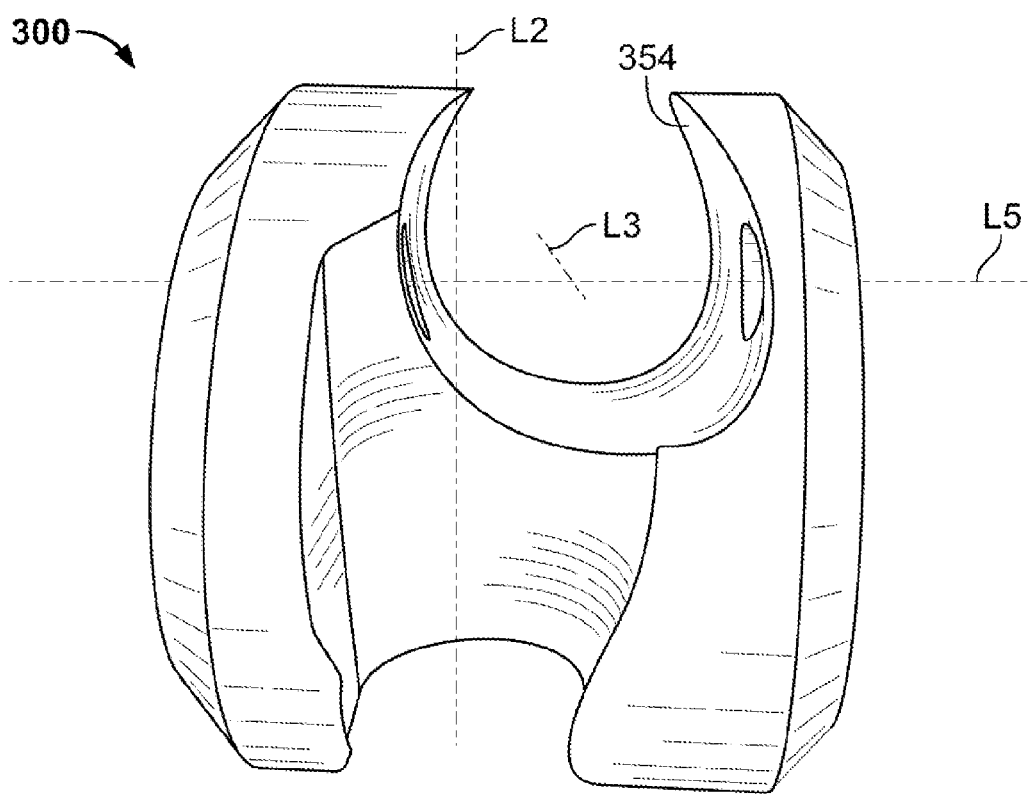
FIG. 4C is another plan view of the housing shown in FIG. 4A in which the bore for receiving the elongate rod and a bore for receiving the actuation member therethrough are shown.

FIGS. 4A-4C show several views of housing 300. Housing 300 includes first and second side surfaces 310, 320 and a generally rounded outer circumference surface 330. Housing 300 includes a first bore 340 having a longitudinal axis L2 and a second bore 350 having a longitudinal axis L3. Longitudinal axes L2 and L3 are angled and offset with respect to one another.

First bore 340 is at least partially bounded by a flat wall portion 342 and a circular wall portion 344 and a lip portion 346 projecting outwardly from flat wall portion 342 as shown in FIG. 4B. Second bore 350 is at least partially bounded by a circular wall portion 354 as shown in FIG. 4C.

Housing 300 further includes a third bore 360 having a longitudinal axis L5 perpendicular to longitudinal axis L2 of first bore 340. Third bore 360 extends through first and second side surfaces 310, 320 of housing 300.

FIGS. 5A-5D show several views of actuation member 400. Actuation member 400 includes a gear portion 420, a neck portion 424, a shoulder portion 428 and an actuation portion 440. Gear portion 420 is located at a distal portion 430 of actuation member 400 and the actuation portion 440 is located at a proximal portion 432 of actuation portion 440.

A plurality of tooth portions 450 extend from a central portion 460 of gear portion 420 adjacent a central longitudinal axis L4 of actuation member 400 towards an outer periphery 465 of gear portion 420. Each of the plurality of tooth portions 450 are curved in a first direction from central portion 460 of gear portion 420 towards outer periphery 465 of gear portion 420. Each of the plurality of tooth portions 450 are also curved in a second direction from distal portion 430 of actuation member 440 towards proximal portion 432 of actuation member 440.

Figures 5A, 5B:
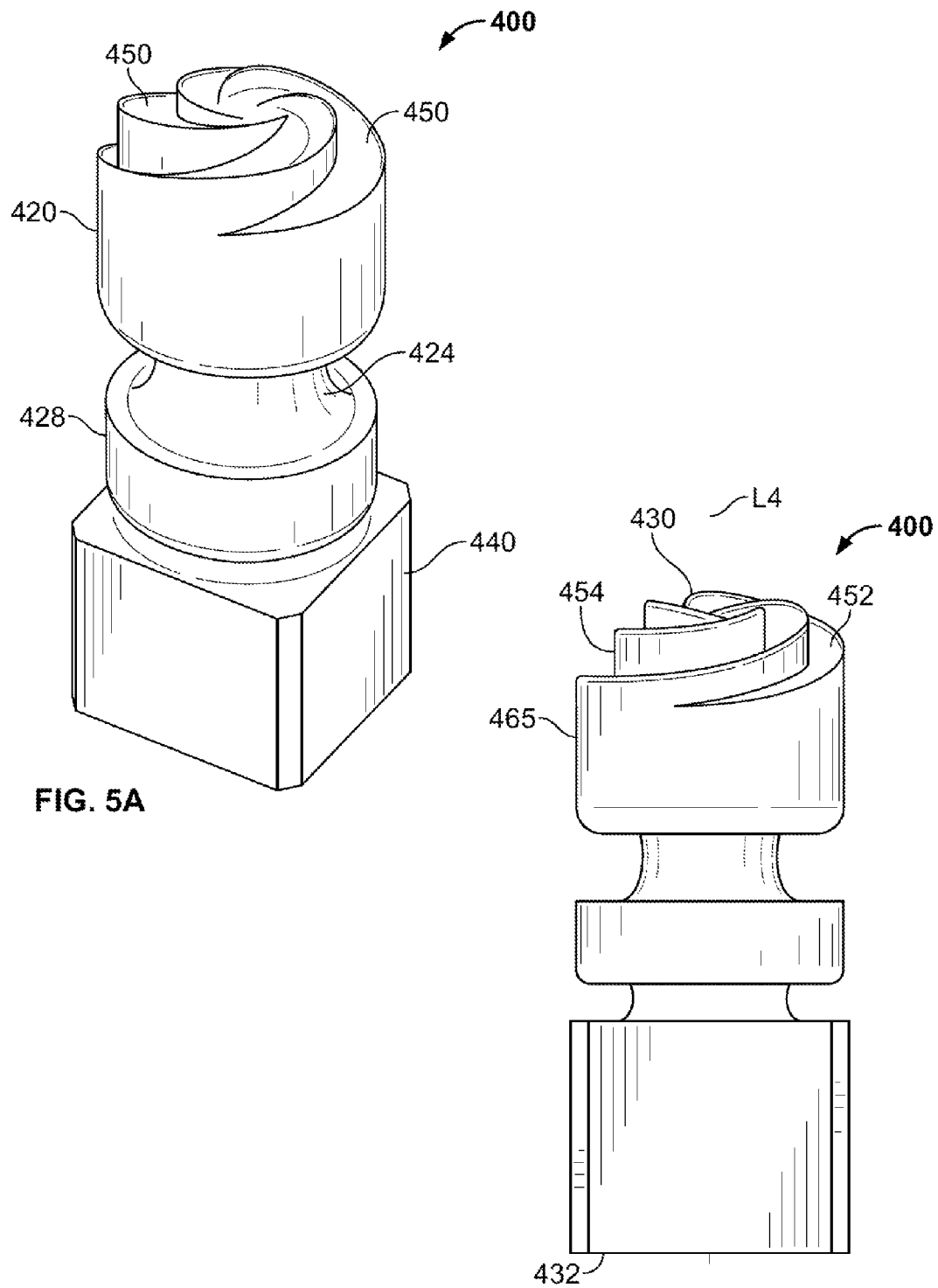
FIG. 5A is a perspective view of the actuation member shown in FIG. 1.
FIG. 5B is a side plan view of the actuation member of FIG. 5A.
Figure 5C:
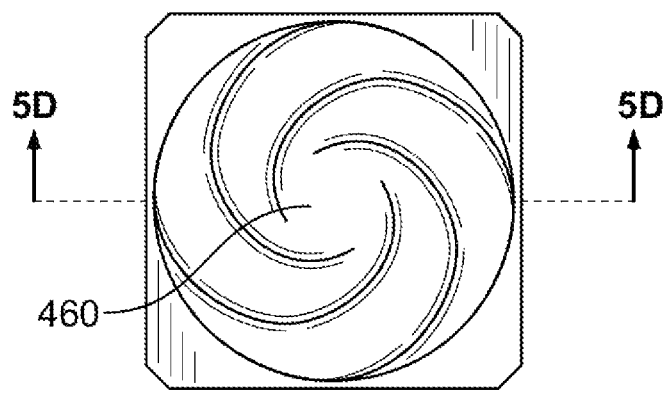
FIG. 5C is a top plan view of the actuation member of FIG. 5A.
Figure 5D:
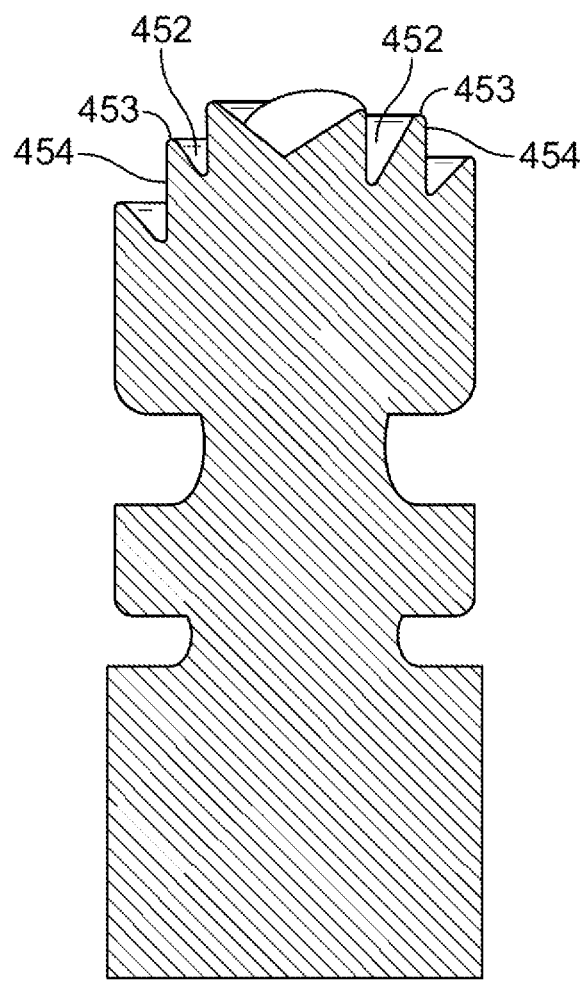
FIG. 5D is a cross-sectional view of the actuation member of FIG. 5A taken along line 5D-5D of FIG. 5C.
Figure 6:
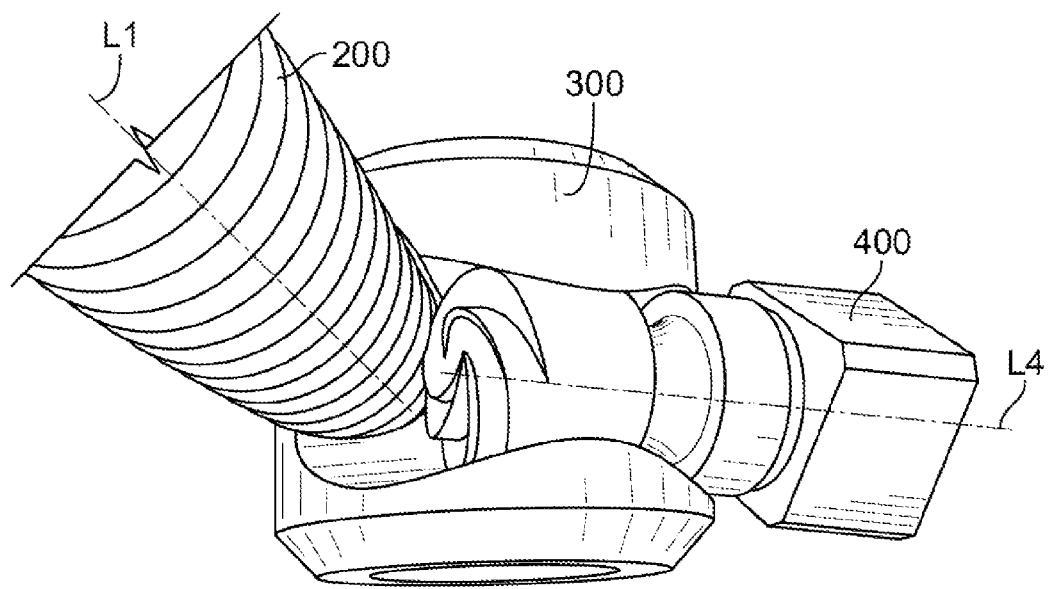
FIG. 6 is another perspective assembled view of the external fixation device of FIG. 1 showing the longitudinal axes of the elongate rod and actuation member being angled and offset from one another.

As shown in the cross-sectional view of actuation member 400 in FIG. 5D, a first contact surface 452 and a second contact surface 454 is provided on each of the plurality of tooth portions 450. First and second contact surfaces 452, 454 are angled with respect to one another and are preferably flat surfaces. In other embodiments, first contact surface 452 may be curved or parabolic. First and second contact surfaces 452, 454 preferably intersect at a peak portion 453 for each tooth portion 450. Peak portion 453 may be sharp or rounded. Second contact surface 454 of each of the plurality of tooth portions 450 has a longitudinal axis L5 that is parallel to the central longitudinal axis L4 of actuation member 400 as shown in FIG. 5B.

Gear portion 420 preferably includes four tooth portions 450 extending from central portion 460 of gear portion 420 separated 90° from one another about central longitudinal central axis L4 of actuation member 400. Gear portion 420 is preferably circular. In some embodiments, gear portion 420 may include more or less than four tooth portions 450. In such embodiments, tooth portions 450 may extending from central portion 460 of gear portion 420 by more or less than 90° from one another about central longitudinal central axis L4 of actuation member 400.

In use, elongate rod 200 is coupled to housing 300 by sliding an end of elongate rod 200 into first bore 340 of housing 300 by lining up flat portion 240 of elongate rod 200 and flat wall portion 342 of housing 300 as well as curved portion 230 of elongate rod 200 and curved wall portion 344 of housing 300. Actuation member 400 is then coupled to housing 300 by sliding distal portion 430 of actuation member 400 into second bore 350 of housing 300 by lining up the circular outer surface of distal portion 430 of actuation member 400 and circular wall portion 354 of second bore 350. Actuation member 400 is received into second bore 350 until a portion of the tooth portions 450 of gear portion 420 thereof comes in contact with the threads of threaded elongate rod 200.

In order to maintain the coupling of actuation member 400 and housing 300 as well as the contact between tooth portions 450 of gear portion 420 and the threads of threaded elongate rod 200, a post member 480 is received within third bore 360 and lies adjacent first and second side surfaces 310, 320 of housing 300. When coupled to housing 300, post member 480 spans at least a portion of curved wall portion 354 of second bore 350 and is received within a recess of neck portion 424 of actuation member 400. Post member 480 precludes actuation member 400 from translating along longitudinal axis L3 of second bore 350.

Actuation member 400 is rotatably coupled to housing 300 such that central longitudinal axis L4 thereof is angled and offset with respect to central longitudinal axis L1 of elongate rod 200. Rotation of actuation portion 440 of actuation member 400 about central longitudinal axis L4 thereof in a first radial direction causes housing 300 to translate along central longitudinal axis L1 of elongate rod 200 in a first direction. Rotation of actuation portion 440 of actuation member 400 about central longitudinal axis L4 thereof in a second radial direction opposite the first radial direction causes housing 300 to translate along central longitudinal axis L1 of elongate rod 200 in a second direction opposite the first direction.

External fixation device 100 can be incorporated into other fixation device constructs in order to achieve a desired clinical outcome. For example, external fixation rods and clamps may be used to stabilize a hip fracture in the ilium, for example. In such a case, a pelvic frame may be used. Elongate rods used to treat this area generally span the iliac crest. While stabilization of bone fragments is generally a key factor in treating a trauma situation or in healing after a surgical procedure is performed, there exists a need at times for compression to be applied to the fracture site in order for bone regeneration and solidification of bone fragments to occur. By coupling external fixation device 100 to a pelvic frame, for example, the position of the rods thereof and the clamps attached thereto may be manipulated in order to apply compression to the ilium. Alternatively, external fixation device 100 can be used for limb lengthening, for example, as well as compression when coupled to external fixation devices attached to long bones such as the tibia or femur.

Figure 7:
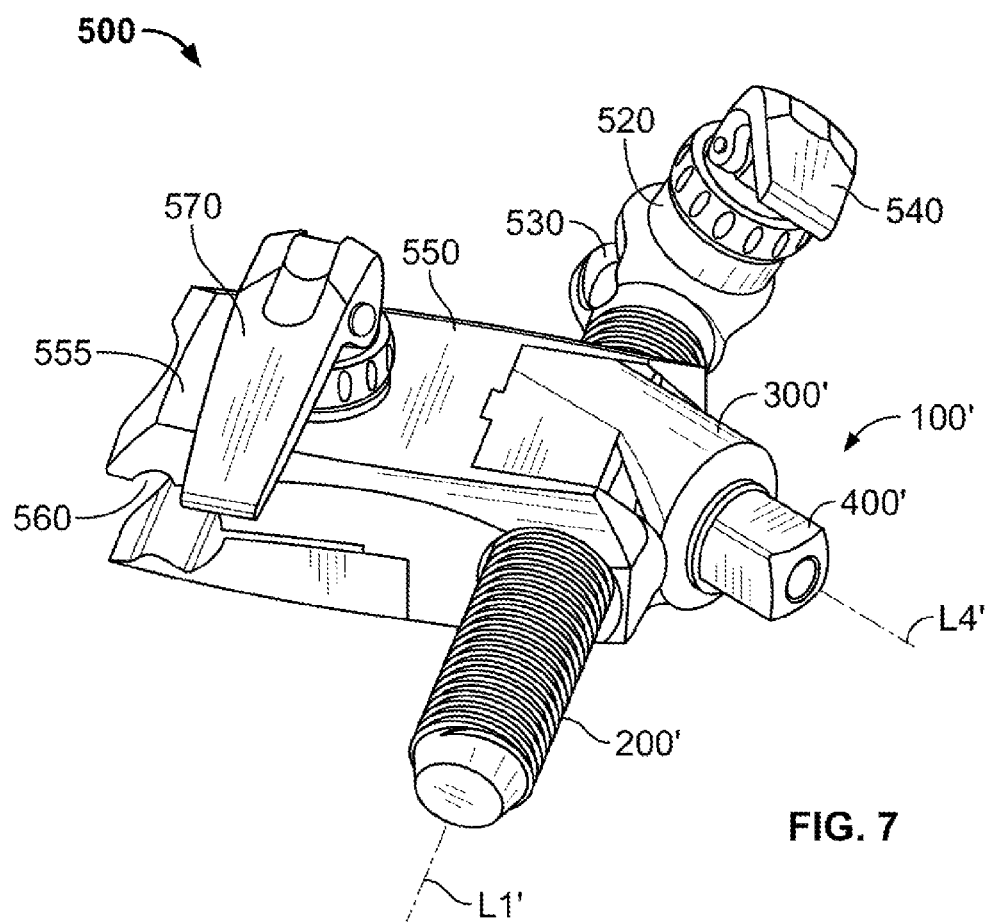
FIG. 7 is a perspective view of an external fixation system of the present invention including another embodiment of an external fixation device and additional external fixation devices coupled thereto.

FIG. 7 is a perspective view of an external fixation system 500 of the present invention including another embodiment of an external fixation device 100' coupled to an additional external fixation device such as body member 550. There, like numerals refer to like elements, except that the reference numbers are expressed in primes. External fixation device 100' includes a threaded rod 200', a housing 300', and an actuation member 400'. Rotation of the actuation member 400' provides the torque transfer to threaded rod 200' needed to translate threaded rod 200' with respect to housing 300'. The open face rose gear design of the distal portion of actuation member 400' allows the actuation member 400' to be angled with respect to threaded rod 200' and not allow for any backdrive of the threaded rod 200.' Without rotation of the actuation member 400', the threaded rod 200' maintains its position with respect to housing 300.'

As shown in FIG. 7, a portion of a perimeter of housing 300' is coupled to a recess in body 550. At least a portion of threaded rod 200' having a longitudinal axis L1' is received and housed within a first bore of housing 300' and a first bore of body 550. At least a portion of actuation member 400' having a longitudinal axis L4' is received and housed within housing 300'. Longitudinal axes L1' and L4' are angled and offset with respect to one another.

A first coupling mechanism 520 is coupled at an end of threaded rod 200' and body 550 includes a second coupling mechanism 555. First and second coupling mechanisms each include a recess 530, 550 and a clamping device 540, 570 respectively. Recesses 530, 550 are each configured to receive and at least partially house a fixation rod therein. Clamping devices 540, 570 each include a lever for effecting the width of recesses 530, 550. When the lever of each clamping device 540, 570 is in an open position, a rod may be slid into a desired position within recesses 530, 550. When in a closed position, the position of the rod within recesses 530, 550 is fixed.

Figure 10:
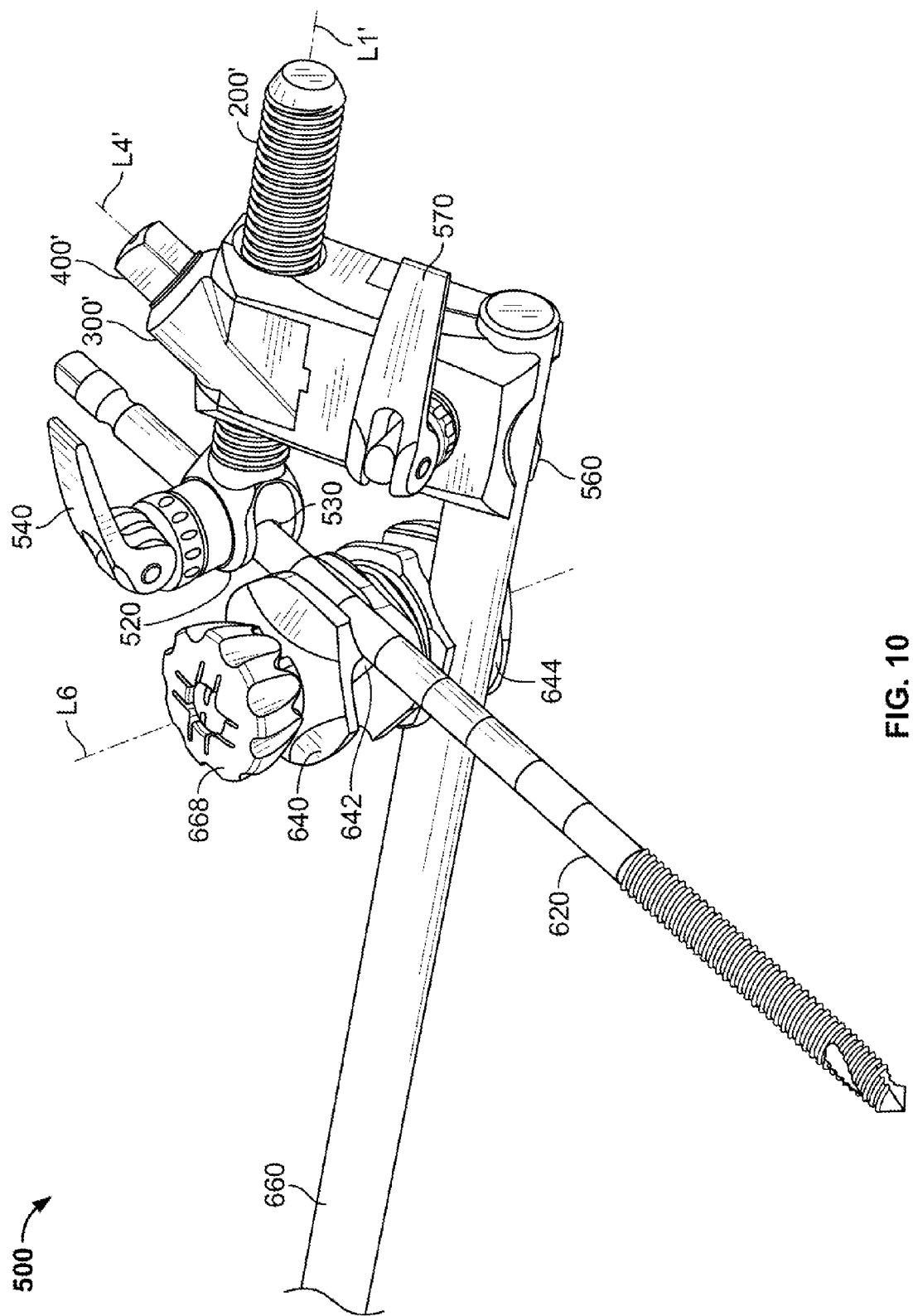
FIG. 10 is a perspective view of still yet another external fixation system of the present invention including the embodiment of the external fixation device of FIG. 7 and additional external fixation devices coupled thereto.

As shown in FIG. 10, external fixation system 500 further includes a fixation pin 620, a clamp 640 and a fixation rod 660. Fixation pin 620 is at least partially received within recess 530 of first coupling mechanism 520 and fixation pin 620 is also at least partially received within a first fixation rod receiving recess 642 in clamp 640. A fixation rod 680 is at least partially received within a second fixation rod receiving recess 644 in clamp 640 and is also at least partially received within recess 555 of body member 550. Thumb wheel 668 of clamp 640 is rotated about a longitudinal axis L6 of clamp 640 in first and second directions in order to tighten or free the grip of fixation pin 620 in first fixation rod receiving recess 642 in clamp 640 as well as fixation rod 680 in second fixation rod receiving recess 644 in clamp 640.

In use, actuation member 400' is rotated about central longitudinal axis L4 thereof in a first radial direction causing threaded rod 200' to translate with respect to housing 300' in a first direction. Rotation of actuation 400' about central longitudinal axis L4 thereof in a second radial direction opposite the first radial direction causes threaded rod 200' to translate with respect to housing 300' in a second direction opposite the first direction. Translation of threaded rod 200' with respect to housing 300' will also translate recess 530 of clamping mechanism 520 in first and second directions following the movement of threaded rod 200'.

Because of the integrated design of external fixation device 100', even with one or both of levers of clamping device 540, 570 in a closed position, coupling mechanism 520 housing at least a portion of a fixation pin as shown in FIG. 10 will also move in the first and second directions as well. Rotation of thumb wheel 668 of clamp 640 may be needed to free the grip of fixation pin 620 in first fixation rod receiving recess 642 in clamp 640 as well as fixation rod 680 in second fixation rod receiving recess 644 in clamp 640 in order to have clamp 640 translate along fixation rod 680. Once clamp 640 is in a desired position with respect to fixation rod 680, the thumb wheel 668 of clamp 640 can be tightened and external fixation device 100' can be removed from fixation pin 620 and fixation rod 640, if desired by lifting the levers of clamping device 540, 570.

Figure 8:
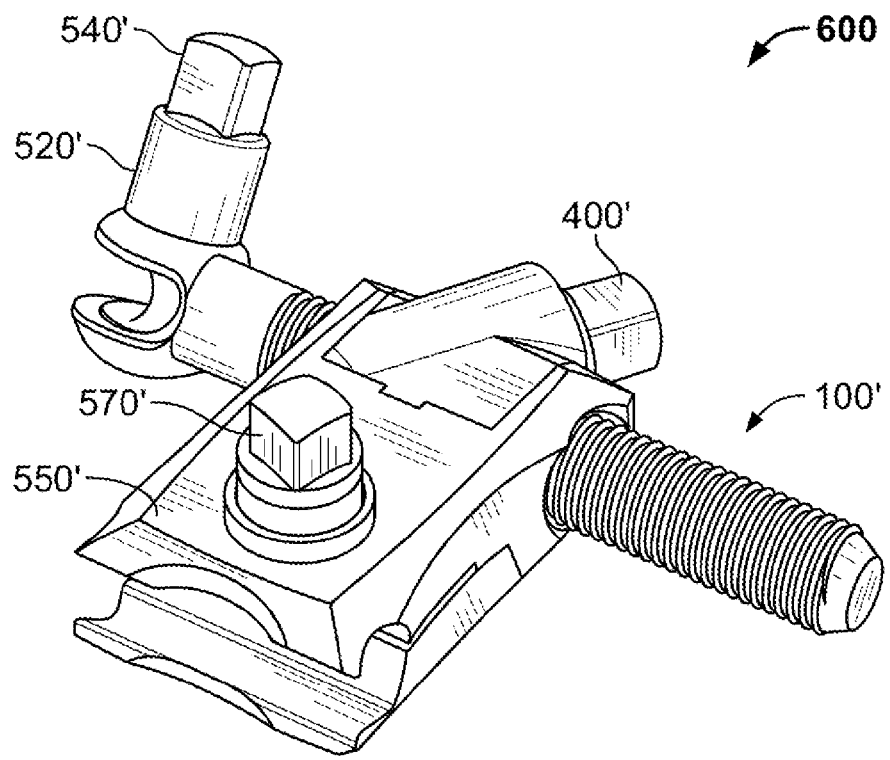
FIG. 8 is a perspective view of another external fixation system of the present invention including the embodiment of the external fixation device of FIG. 7 and additional external fixation devices coupled thereto.

FIG. 8 is a perspective view of another external fixation system 600 of the present invention including external fixation device 100' and additional external fixation devices coupled thereto. There, like numerals refer to like elements, except that the reference numbers are expressed in primes. A first coupling mechanism 520' is coupled at an end of threaded rod 200' and body 550' includes a second coupling mechanism 555'. First and second coupling mechanisms each include a recess 530', 550' and a clamping device 540', 570' respectively'. Recesses 530', 550' are each configured to receive and at least partially house a fixation pin or rod therein as shown in FIG. 10, for example. Clamping devices 540', 570' each include a rotatable actuation portion for effecting the width of recesses 530', 550'. When the actuation portion of each clamping device 540', 570' is rotated in first direction, a pin or rod may be slid into a desired position within recesses 530', 550'. When the actuation portion is rotated in a second direction, the position of the pin or rod within recesses 530', 550' is fixed.

Figure 9:
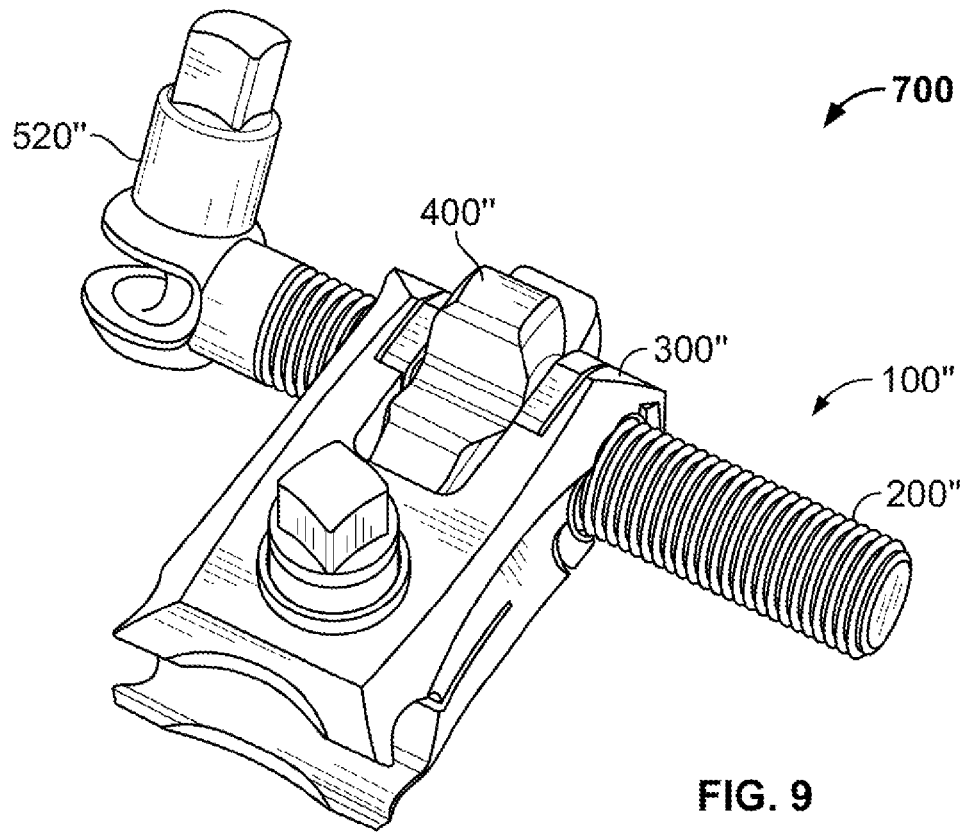
FIG. 9 is a perspective view of yet another external fixation system of the present invention including another embodiment of an external fixation device and additional external fixation devices coupled thereto.

FIG. 9 is a perspective view of yet another external fixation system 700 of the present invention including another embodiment of an external fixation device 100" and additional external fixation devices coupled thereto. There, like numerals refer to like elements, except that the reference numbers are expressed in primes. External fixation device 100" includes a threaded rod 200", a housing 300", and an actuation member 400". Actuation member 400" is coupled to housing 300" differently than other actuation members are coupled to other housings of the previous embodiments described herein. In this embodiment, actuation member 400" has an inner gear surface that cooperates with the threads of threaded rod 200". Actuation member 400" is configured to rotate coaxially about a longitudinal axis of threaded rod 200". Rotation of the actuation member 400" provides the torque transfer to threaded rod 200' needed to translate threaded rod 200" with respect to housing 300". Rotation of actuation member 400" about longitudinal axis L1" of housing 300" causes threaded rod 200" to translate with respect to housing 300".

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An external fixation device comprising:
an elongate rod having threads and a central longitudinal axis;
a housing coupled to the elongate rod; and
an actuation member rotatably coupled to the housing such that a central longitudinal axis thereof is both angled in a non-orthogonal orientation and offset with respect to the central longitudinal axis of the elongate rod, the actuation member having a gear portion and an actuation portion, the gear portion being located on a distal end surface of the actuation member,
wherein rotation of the actuation portion of the actuation member about the central longitudinal axis thereof in a first radial direction causes the elongate rod to translate with respect to the housing in a first direction by the interaction of the gear portion of the actuation member and the threads of the elongate rod.

2. The external fixation device of claim 1, wherein rotation of the actuation portion of the actuation member about the central longitudinal axis thereof in a second radial direction opposite the first radial direction causes the elongate rod to translate with respect to the housing in a second direction opposite the first direction.

3. The external fixation device of claim 1, wherein the actuation portion is located at a proximal portion of the actuation member.

4. The external fixation device of claim 3, wherein the gear portion has a plurality of tooth portions extending from a central portion of the gear portion adjacent the central longitudinal axis of the actuation member towards an outer periphery of the gear portion.

5. The external fixation device of claim 4, wherein each of the plurality of tooth portions are curved in a first direction from the central portion of the gear portion towards the outer periphery of the gear portion.

6. The external fixation device of claim 5, wherein each of the plurality of tooth portions are curved in a second direction from the distal portion of the actuation member towards the proximal portion of the actuation member.

7. The external fixation device of claim 4, wherein each of the plurality of tooth portions has first and second contact surfaces, the first and second contact surfaces being angled with respect to one another, wherein one of the first and second contact surfaces has a longitudinal axis parallel to the central longitudinal axis of the actuation member.

8. The external fixation device of claim 7, wherein the first and second contact surfaces are flat.

9. The external fixation device of claim 4, wherein the gear portion includes four tooth portions extending from the central portion of the gear portion separated 90° from one another about the longitudinal central axis of the actuation member.

10. The external fixation device of claim 1, wherein the housing has first and second bores, the elongate rod being at least partially received in the first bore when the elongate rod is coupled to the housing and the actuation member being at least partially received in the second bore when the actuation member is rotatably coupled to the housing.

11. The external fixation device of claim 10, wherein each of the first and second bores has a longitudinal axis, the longitudinal axes of the first and second bores being angled and offset with respect to one another.

12. The external fixation device of claim 1, wherein the housing includes first and second bores, the elongate rod being received in the first bore to couple the elongate rod to the housing and the actuation member being received in the second bore to couple the actuation member to the housing.

13. An external fixation device comprising:
a housing having first and second bores, each having a longitudinal axis that are both angled in a non-orthogonal orientation and offset with respect to one another;
an elongate rod having threads and a central longitudinal axis and being adapted to be at least partially received in the first bore of the housing; and
an actuation member having a central longitudinal axis being adapted to be at least partially received in the second bore of the housing, the actuation member having a gear portion and an actuation portion, the gear portion being located on a distal end surface of the actuation member,
wherein rotation of the actuation portion of the actuation member about the central longitudinal axis thereof in a first radial direction causes the housing and threaded elongate rod to translate with respect to one another about the central longitudinal axis of the threaded elongate rod in a first direction by the interaction of the gear portion of the actuation member and the threads of the elongate rod.

14. The external fixation device of claim 13, wherein rotation of the actuation portion of the actuation member about the central longitudinal axis thereof in a second radial direction opposite the first radial direction causes the housing and threaded elongate rod to translate with respect to one another about the central longitudinal axis of the elongate rod in a second direction opposite the first direction.

15. The external fixation device of claim 13, wherein the actuation portion is located at a proximal portion of the actuation member.

16. The external fixation device of claim 15, wherein the gear portion has a plurality of tooth portions extending from a central portion of the gear portion adjacent the central longitudinal axis of the actuation member towards an outer periphery of the gear portion.

17. The external fixation device of claim 16, wherein each of the plurality of tooth portions are curved in a first direction from the central portion of the gear portion towards the outer periphery of the gear portion.

18. The external fixation device of claim 17, wherein each of the plurality of tooth portions are curved in a second direction from the distal portion of the actuation member towards the proximal portion of the actuation member.

19. The external fixation device of claim 16, wherein each of the plurality of tooth portions has first and second contact surfaces, the first and second contact surfaces being angled with respect to one another, wherein one of the first and second contact surfaces has a longitudinal axis parallel to the central longitudinal axis of the actuation member.

20. The external fixation device of claim 19, wherein the first and second contact surfaces are flat.

21. The external fixation device of claim 16, wherein the gear portion includes four tooth portions extending from the central portion of the gear portion separated 90° from one another about the longitudinal central axis of the actuation member.

\* \* \* \* \*